(12) United States Patent
Dong

(10) Patent No.: US 7,208,125 B1
(45) Date of Patent: Apr. 24, 2007

(54) METHODS AND APPARATUS FOR MINIMIZING EVAPORATION OF SAMPLE MATERIALS FROM MULTIWELL PLATES

(75) Inventor: Wesley Bryan Dong, Belmont, CA (US)

(73) Assignee: Caliper Life Sciences, Inc, Mountain View, CA (US)

( * ) Notice: Subject to any disclaimer, the term of this patent is extended or adjusted under 35 U.S.C. 154(b) by 661 days.

(21) Appl. No.: 10/606,203

(22) Filed: Jun. 25, 2003

Related U.S. Application Data

(60) Provisional application No. 60/392,210, filed on Jun. 28, 2002.

(51) Int. Cl.
    B01L 3/00     (2006.01)
    G01N 1/00     (2006.01)
    G01N 21/00    (2006.01)
    C12M 1/22     (2006.01)

(52) U.S. Cl. .......................... 422/102; 422/58; 422/99; 422/104; 436/174; 435/305.3; 435/305.4

(58) Field of Classification Search ................. 422/50, 422/58, 60; 435/305.1, 305.2, 305.3, 305.4
    See application file for complete search history.

(56) References Cited

U.S. PATENT DOCUMENTS

| 4,657,867 A |   | 4/1987  | Guhl et al. |            |
|-------------|---|---------|-------------|------------|
| 4,948,442 A | * | 8/1990  | Manns       | 156/73.1   |
| 5,587,321 A | * | 12/1996 | Smith et al.| 435/305.3  |

(Continued)

FOREIGN PATENT DOCUMENTS

| WO | WO-02/072423 | 9/2002  |
|----|--------------|---------|
| WO | WO-02/087763 | 11/2002 |

(Continued)

*Primary Examiner*—Jill Warden
*Assistant Examiner*—Neil Turk
(74) *Attorney, Agent, or Firm*—Ann C. Peterson; Donald R. McKenna

(57) ABSTRACT

Methods and devices for reducing evaporation of sample materials from the wells of multiwell plates are disclosed which find particular utility when the plates are placed in a stacked configuration. An example of the methods includes providing at least a first multiwell plate which is configured to be placed in a stacked configuration with at least one second multiwell plate, the at least first multiwell plate having a plurality of wells for receiving sample material therein and opposing side walls which extend around the plate and which define a ridge spaced inwardly of the side walls and extending around the plate between the side walls and the plurality of wells, the method including at least partially filling the ridge with a liquid such as water or buffer solution. The ridge can include one or more ribs which extend upwardly from a lower surface of the ridge to help reduce sloshing of the liquid contained within the ridge and to add structural strength and rigidity to the multiwell plate. The second multiwell plate can be provided with a downwardly extending flange which extends around a lower surface of the plate and which is configured to be removably received by the ridge of the at least first multiwell plate such that when the second multiwell plate is removably positioned on top of the at least first multiwell plate in a stacked configuration, the flange extends at least partially into the ridge and contacts the liquid to thereby create a substantial evaporation barrier to minimize evaporation of sample liquids in the wells of the at least first multiwell plate.

9 Claims, 5 Drawing Sheets

U.S. PATENT DOCUMENTS

| | | | |
|---|---|---|---|
| 5,741,463 A * | 4/1998 | Sanadi | 422/101 |
| 5,789,251 A | 8/1998 | Astle | |
| 5,908,776 A * | 6/1999 | Burbaum et al. | 435/288.3 |
| 5,942,443 A | 8/1999 | Parce et al. | |
| 5,955,352 A * | 9/1999 | Inoue et al. | 435/287.7 |
| 6,018,388 A * | 1/2000 | Nawracala et al. | 356/246 |
| 6,074,614 A | 6/2000 | Hafeman et al. | |
| 6,132,685 A | 10/2000 | Kercso et al. | |
| 2001/0001644 A1 * | 5/2001 | Coffman et al. | 422/102 |

\* cited by examiner

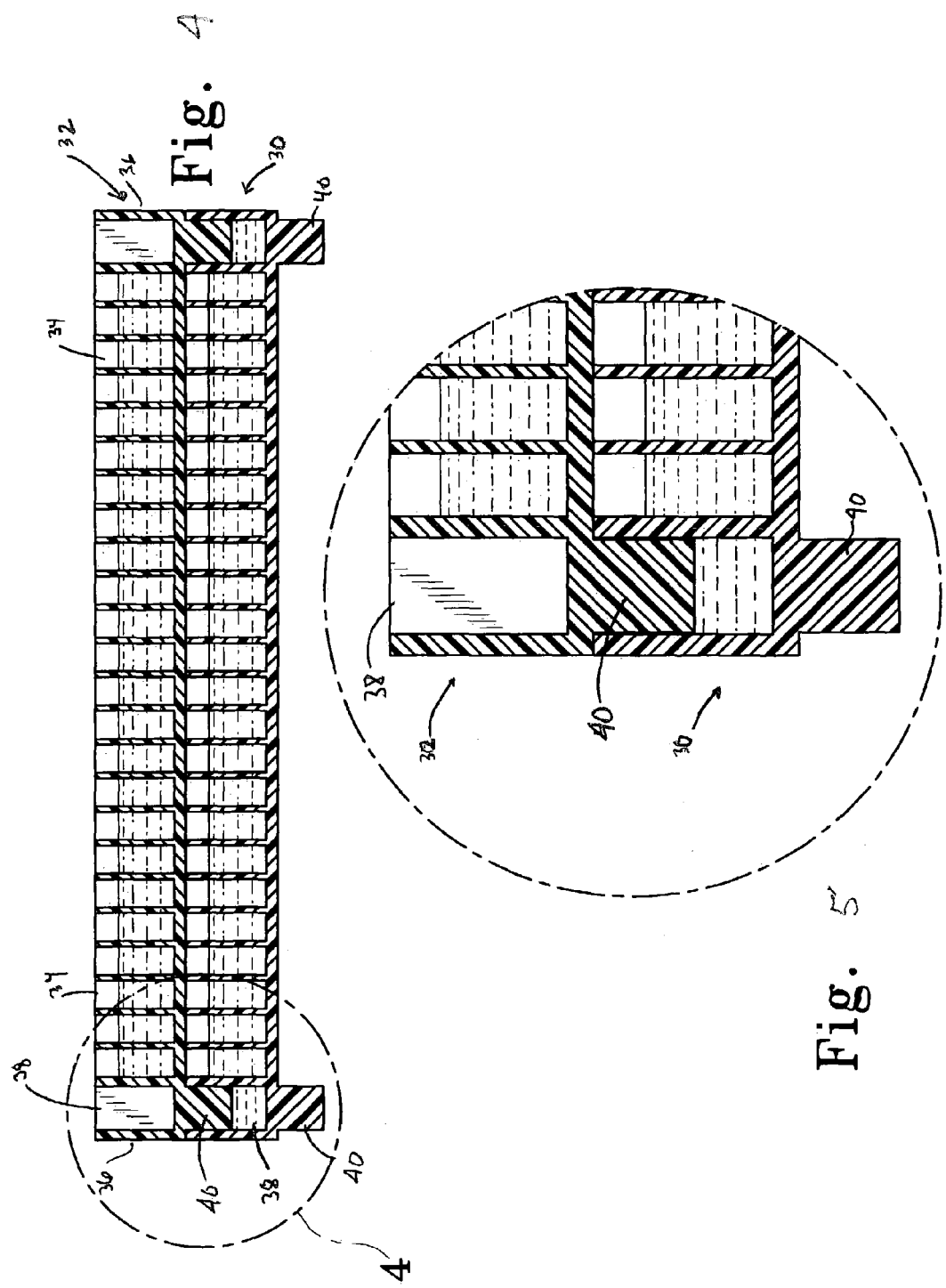

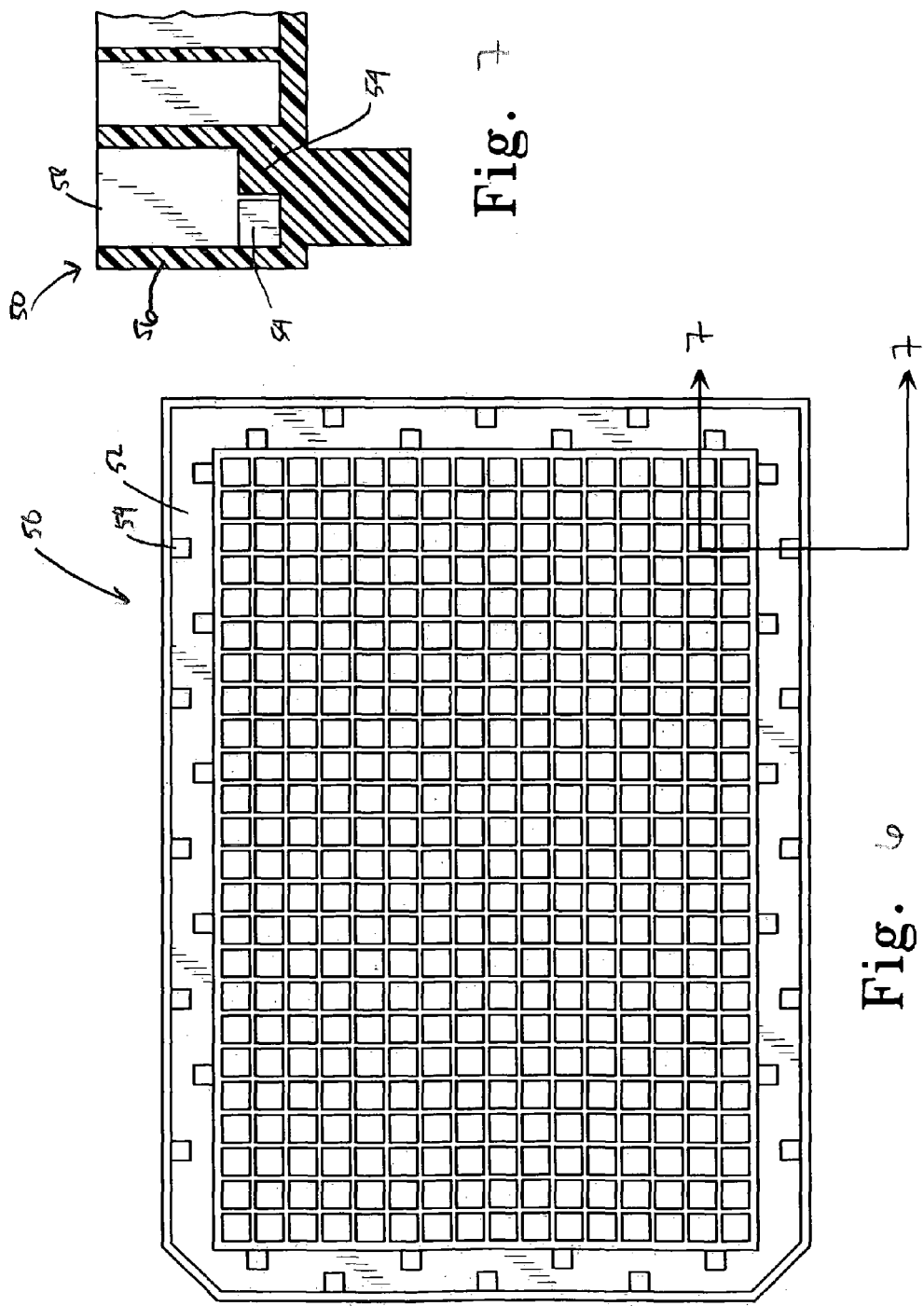

METHODS AND APPARATUS FOR MINIMIZING EVAPORATION OF SAMPLE MATERIALS FROM MULTIWELL PLATES

CROSS-REFERENCE TO RELATED APPLICATIONS

This application claims the benefit of U.S. Provisional Patent Application No. 60/392,210, filed Jun. 28, 2002, which is incorporated herein by reference in its entirety for all purposes.

FIELD OF THE INVENTION

The present invention relates to multiwell plates for storing sample materials, and more particularly, to methods and apparatus for minimizing evaporation of sample materials from the wells of such plates, particularly where two or more multiwell plates are stacked one on top of another as they typically are in usage in high-throughput screening systems, for example.

BACKGROUND OF THE INVENTION

Recently, novel high-throughput screening (HTS) devices based on microfluidics technology have been developed which have the capability to rapidly assay compounds for their effects on various biological processes, including, for example, fluorogenic and mobility shift assays for multiple target classes including kinases, proteases and phosphatases, cell-based assay including calcium flux and membrane potential, and the like. See, e.g., U.S. Pat. Nos. 5,942,443 and 6,132,685, both assigned to the assignee of the instant invention, the entire contents of which are incorporated by reference herein. Such HTS systems perform high volume experimentation, on the order of tens of thousands of experiments per microfluidic chip, using nanoliters of reagents. Such systems typically perform experiments in serial, continuous flow fashion and employ a "chip-to-world" interface, or sample access system, called a "sipper" through which test compounds residing in stacked microwell plates are sipped into a capillary or capillaries attached to the chip and drawn into the microfluidic channels of the chip. There they are mixed with the target biomolecule and a series of processing steps is carried out to determine the effect of the compounds on the target. The benefits of systems for high throughput screening are several: decreased time for assay development; assay transfer and hit validation; integrated reagent handling leading to enhanced productivity; significant reductions in compound library use; up to a 100,000-fold reduction in target use for screening; and higher quality, more reproducible results leading to more reliable hit and lead generation.

In operation of such HTS systems, typically multiwell plates containing large numbers of different test compounds are stacked on top of one another in a plate stack and then fed one at a time, e.g., by robotic systems (e.g., x-y or x-y-z-type robotic translation systems), conveyor systems, or the like, to a test area of the system where the samples in the multiple wells of the plates can be accessed by one or more sippers extending from the microfluidic chip, such that the test compounds can be sampled into the chips, e.g., interspersed by appropriate spacer fluid regions. After loading the test compounds into the chips, the multiwell plates are then collected or stacked at an opposite end of the system for retrieval.

The inventor has recognized that currently available multiwell plates often permit too much air to flow to the wells from the external environment. In a larger multiwell plate such as a 96 or 384 well plate, for example, such air exchange generally causes no problems with respect to the samples in the interior wells. However, those wells around the periphery or the corners of the multiwell plate are disturbed by excess airflow from the external environment because those wells have an interface to the ambient environment where the plate handling equipment is located. Conversely, the interior wells of the plate "see" an environment that is essentially saturated with water vapor (until the perimeter wells completely evaporate). Thus, evaporation theoretically proceeds in a stepwise fashion. That is, the perimeter wells evaporate completely before the interior wells show appreciable evaporation. Excess air causes the evaporation of samples from wells, which is an issue for the performance of assays, particularly in HTS systems, where run times may be on the order of eight hours or more. Samples must then either be replenished more frequently to compensate for evaporation, or the peripheral or corner wells filled with water or buffer and not used for the assays, which reduces the high throughput capabilities of the system.

To combat the problem of evaporation from multiwell plates, many conventional multiwell plates are designed with lids for covering the plates. An example of such a multiwell plate with lid assembly is exemplified in U.S. Pat. No. 4,657,867. Other multiwell plates use some form of a layer or membrane which is disposed over the vertical wells to prevent the evaporation of liquid therefrom, wherein the layer of film is penetrable, for example, by a pipette tip or the like to access one of the vertical wells to add liquid to or withdraw liquid from the well, as is described in U.S. Pat. No. 5,789,251, for example. However, in usage of HTS systems as described above, where multiwell plates are stacked one on top of another and must be readily and easily accessible by robotic systems and the like, the use of a separate lid or membrane to reduce evaporation is cumbersome and difficult to incorporate into the system.

Accordingly, when multiwell plates are stored in a stacked configuration (or even stored unstacked), as they typically are in usage in HTS systems, there is a need for a multiwell plate(s) which is capable of reducing the air flowing to the wells, so as to minimize evaporation of sample from the wells, particularly those wells which are located on the perimeter of the multiwell plate, while still allowing the wells to be readily accessible by automated sipper devices and the like using robotic systems typically employed in HTS systems. The present invention is directed to such multiwell plates which solve the above-described problems.

BRIEF SUMMARY OF THE INVENTION

Novel methods and devices are disclosed for eliminating the problem of evaporation from sample wells of one or more multiwell plates, particularly when such multiwell plates are placed a stacked configuration as is typical in usage in HTS systems.

In a first aspect of the present invention, a method of reducing evaporation from one or more wells of at least a first multiwell plate is disclosed which comprise providing at least the first multiwell plate with a plurality of wells and opposing side walls which extend around the plate and which define a ridge spaced inwardly of the side walls and extending around the plate between the side walls and the plurality of wells, and at least partially filling the ridge with a liquid.

In a related aspect of the present invention, a method of reducing evaporation from one or more wells of at least a first multiwell plate which is configured to be positioned in a stacked configuration with at least one second multiwell plate is disclosed, which method includes providing at least the first multiwell plate with a plurality of wells and opposing side walls which extend around the plate and which define a ridge or channel spaced inwardly of the side walls and extending around the plate between the side walls and the plurality of wells; and at least partially filling the ridge with a liquid. In a preferred aspect of the invention, the second multiwell plate can include a downwardly extending flange which extends around a lower surface of the plate and which is configured to be removably received by the ridge of the at least first multiwell plate, such that when the second multiwell plate is positioned on the first multiwell plate, the flange extends at least partially into the ridge and contacts the liquid to thereby create a substantial evaporation barrier to prevent air exchange to the wells of the first multiwell plate and hence substantially eliminate evaporation of liquids contained therein when the plates are placed in a stacked configuration. The flange, when placed in the ridge of the first multiwell plate and made to contact the liquid contained therein, increases the vapor diffusion path length to the internal wells of the first multiwell plate and thereby slows evaporation of the buffer or other liquids contained within those wells. The flange could also be dimensioned to extend below the liquid level in the ridge, thus forming a "waterlock", substantially preventing air movement to the peripheral wells of the first multiwell plate until the water in the ridge evaporates below the level of the flange of the second multiwell plate. The second multiwell plate may optionally not include a flange, such that when placed on top of the first multiwell plate, the second multiwell plate merely acts as a lid which helps to contain the liquid with the ridge of the first multiwell plate, which in some instances may be sufficient to substantially prevent or reduce evaporation of liquid sample contained with the wells of the multiwell plate(s).

The liquid introduced into the ridge can comprise water, buffer, or other suitable liquid which becomes a substantial evaporation barrier when the plates are stacked to substantially prevent air entrance to the wells to minimize evaporation of liquids in the wells. The liquid within the ridge must evaporate substantially completely before there will be substantial evaporation of the sample liquid contents within the wells of the multiwell plate. The step of at least partially filling the ridge with a liquid step can be performed either before or after the second multiwell plate is removably positioned on the first multiwell plate. A lower surface of the ridge of the first (and second) multiwell plate can optionally be provided with a plurality of spaced-apart ribs or small upwardly extending finger projections or the like which extend upwardly from the ridge and inwardly (e.g., perpendicular to the lengthwise dimension of the ridge) of the opposing side walls of the multiwell plate. The flanges or small projections in the ridge help to minimize sloshing of the liquid contained within the ridge and add structural strength and rigidity to the plate. When used, the upwardly extending ribs preferably have a height which is less than a height of the opposing side walls of the at least first multiwell plate such that a corresponding flange from a second multiwell plate can be placed within the ridge and made to contact the liquid contained therein when the first and second plates are placed in a stack. Further alternatively, the ridge can include a layer of at least one wicking material covering at least a portion of the ridge (or ribs or projections), such as a felt material, or a layer of absorbent material covering at least a portion of the ridge (or ribs or projections), that minimizes the tendency for liquid sloshing during operation of the system and which helps to further reduce evaporation by increasing the surface area of the liquid in the ridge which increases evaporation from the plate wells more effectively.

In a related aspect of the invention, a method of reducing evaporation from one or more wells of at least a first multiwell plate which is configured to be positioned in a stacked configuration with at least a second multiwell plate is provided, which method comprises providing at least a first multiwell plate having a plurality of wells and opposing side walls which extend around the plate and which define a ridge spaced inwardly of the side walls and extending around the plate between the side walls and the plurality of wells; providing at least a second multiwell plate having a downwardly extending flange which extends around a lower surface of the plate and which is configured to be removably received by the ridge of the at least first multiwell plate; at least partially filling the ridge with a liquid; and removably positioning said at least second multiwell plate on said at least first multiwell plate such that the flange extends at least partially into the ridge and contacts the liquid to thereby create a substantial evaporation barrier to prevent air entrance to the wells to minimize evaporation of sample liquids in the wells when the at least second multiwell plate is positioned on the at least first multiwell plate.

In a further related aspect of the invention, a first multiwell plate which is configured to be placed in a stacked configuration with at least one second multiwell plate is disclosed which comprises a plurality of wells for receiving sample material therein, opposing side walls which extend around the plate and which define a ridge spaced inwardly of the side walls and extending around the plate between the side walls and the plurality of wells, and a downwardly extending flange which extends around a lower surface of the plate and which is configured to be removably received by a corresponding ridge of the second multiwell plate when the first multiwell plate is removably positioned on the second multiwell plate in a stacked configuration.

In accordance with the principles of the present invention, significant improvements over currently known and available multiwell plate assemblies are provided. Most importantly, the present invention eliminates or substantially reduces the problem of excessive evaporation of sample material that occurs in multiwell plates, especially when two or more plates are stacked on top of one another as they typically are for use in HTS systems. Sample liquid loss, particularly in the corner or peripheral wells of stacked multiwell plates, may be substantially reduced over current multiwell plate configurations.

BRIEF DESCRIPTION OF THE DRAWINGS

FIG. 4 is a side cross-sectional view of the stacked pair of multiwell plates shown in FIG. 3.

FIG. 5 is an enlarged, partial cross-sectional view of the stacked pair of multiwell plates shown in FIG. 4 taken along dashed circular line 5 of FIG. 4 and showing the mating relationship between the downwardly extending flange and channel assembly of the stacked plates.

FIG. 6 is a top view of an alternative embodiment of the present invention showing a plurality of inwardly extending ribs positioned in the channel of the multiwell plate of FIG. 2.

FIG. 7 is an enlarged, partial cross-sectional view taken along the line 7—7 in FIG. 6, with a partial sectional view of one corner thereof.

DETAILED DESCRIPTION

The present invention provides novel methods and apparatus for minimizing evaporation of sample materials from multiwell plates, particularly when such plates are placed into a stacked configuration with one or more additional multiwell plates as is typical in usage in HTS systems, for example. It is to be understood, however, that the teachings of the present invention are in no way to be limited to their use in HTS systems as are generally described below, but can be used in any system or apparatus in which it is necessary to store one or more multiwell plates in a stacked (or unstacked) configuration prior to sampling of the sample components within the wells of the plates.

Figure 1:
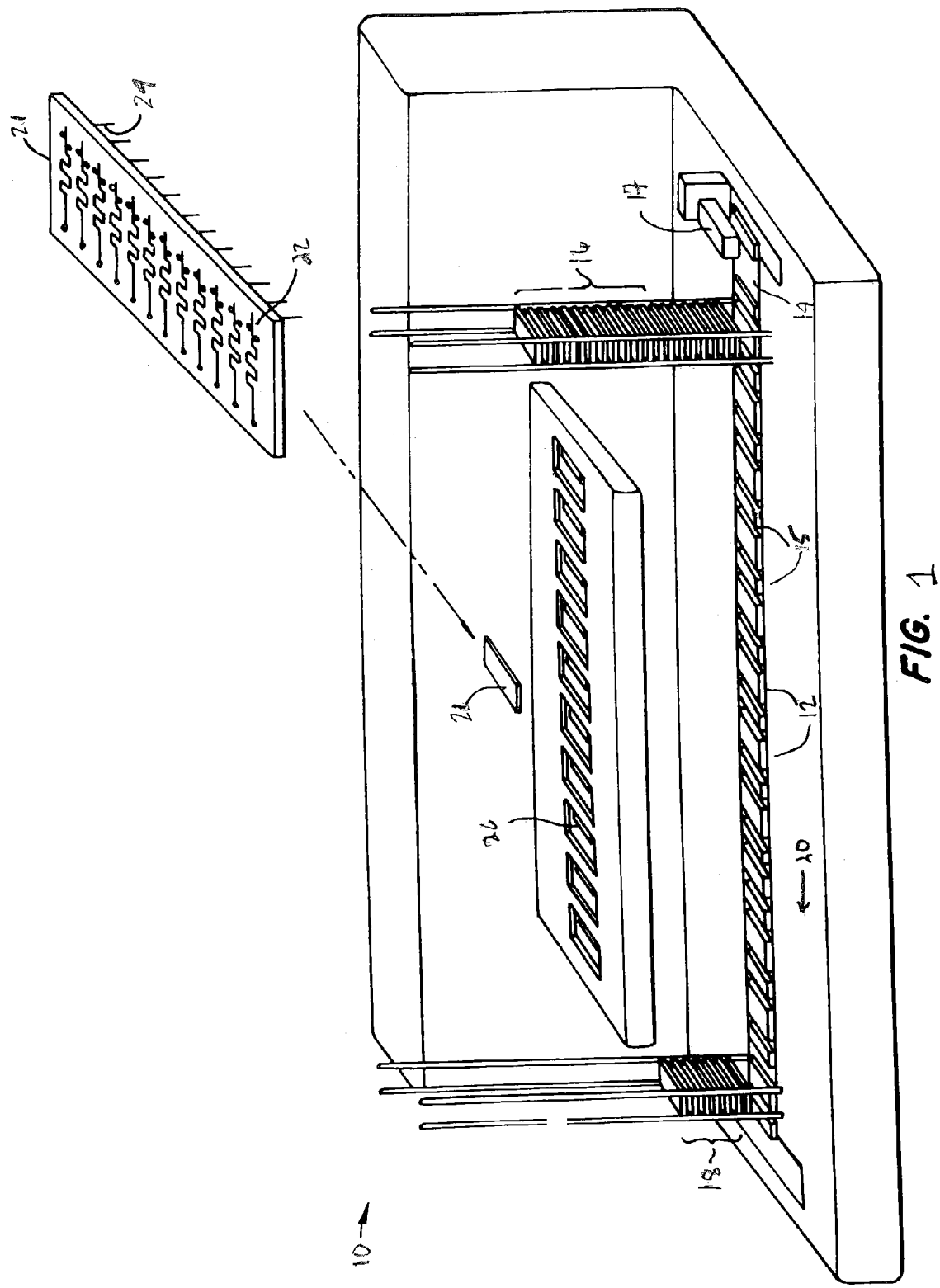
FIG. 1 is a perspective view of an example of a high throughput microfluidic screening (HTS) system which employs at least one stack of multiwell plates which are input into the HTS system one at a time for analysis and sampling of the sample materials in the wells of the multiwell plates.

Referring first to FIG. 1, an exemplary HTS system 10 for screening large numbers of different compounds for their effects in a wide variety of chemical, and particularly biochemical systems, is shown. HTS system 10 generally manipulates samples by translating individual multiwell plates 12, which are arranged in a stacked configuration for ease of accession, along a conveyor system 14 from an input stack 16 to an output stack 18 along a plate path 20. Other plate handling modules which controllably raise and lower plates contained therein and transport the plates to a test station per instruction signals from a processor can be used, such as the Twister or Twister II commercially available from Zymark. The plates are placed upon the conveyor separated by appropriate buffer reservoirs 15, which may be filled by buffer system 17, for example. In the exemplary embodiment shown, the plates 12 are taken individually from input stack 16 and stepped down the conveyor where the test compounds are sampled into the chips 21 (which are placed upon a platform 26, for example, which can hold a number of separate chips), interspersed by appropriate spacer fluid regions. As shown, each chip 21 includes a number of discrete assay channels 22, each having a separate interface 24, e.g., sipper or pipettor, for introducing test compounds into the device. After loading the test compounds into the chips, the multiwell plates are then collected or stacked at outlet stack 18 at the opposite end of the system. Additional information related to the use of such HTS systems and to the various tests conducted on the sample materials using such systems can be found in U.S. Pat. Nos. 5,942,443 and 6,132,685, both assigned to the assignee of the instant invention, the entire contents of which have been previously incorporated by reference herein.

In the exemplary embodiment of the HTS system shown, samples (whether in an immobilized format or liquid form) will be contained in the wells of multiwell plates 12. Conventional multiwell plates typically comprise an array of blind holes or wells, and are commercially available in a variety of forms. For example, 96 well clear polymer plates sold by Corning, Inc. come with an orthogonal 12×8 array of wells, while 384 well plates available commercially from Genetix, for example, have the wells arranged in a 16×24 array. As the multiwell plates in stack 12, for example, await transport to a position below platform 26 where samples within the wells may be accessed by one or more sippers extending from chips 21, sample compounds may evaporate from the wells of such conventional plates when stored for too long in liquid form, particularly for those wells around the periphery or the corners of the multiwell plate which are easily disturbed by excess airflow from the external environment because those wells have an interface to the ambient environment where the plate handling equipment is located. Excess air causes the evaporation of samples from wells which is an issue for the performance of assays, particularly in such HTS systems, where run times may be on the order of eight hours or more.

Figure 2:
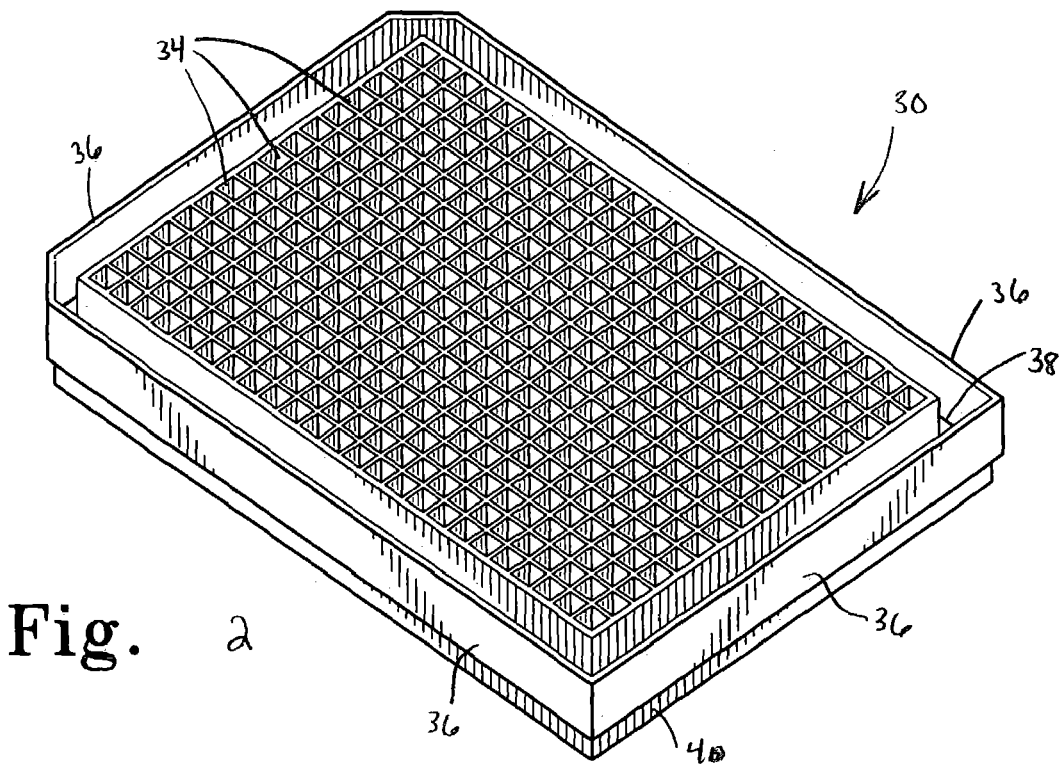
FIG. 2 is a perspective view of one embodiment of a multiwell plate of the present invention illustrating a channel formed between the opposing side walls of the plate and the plurality of sample wells of the plate.
Figure 3:
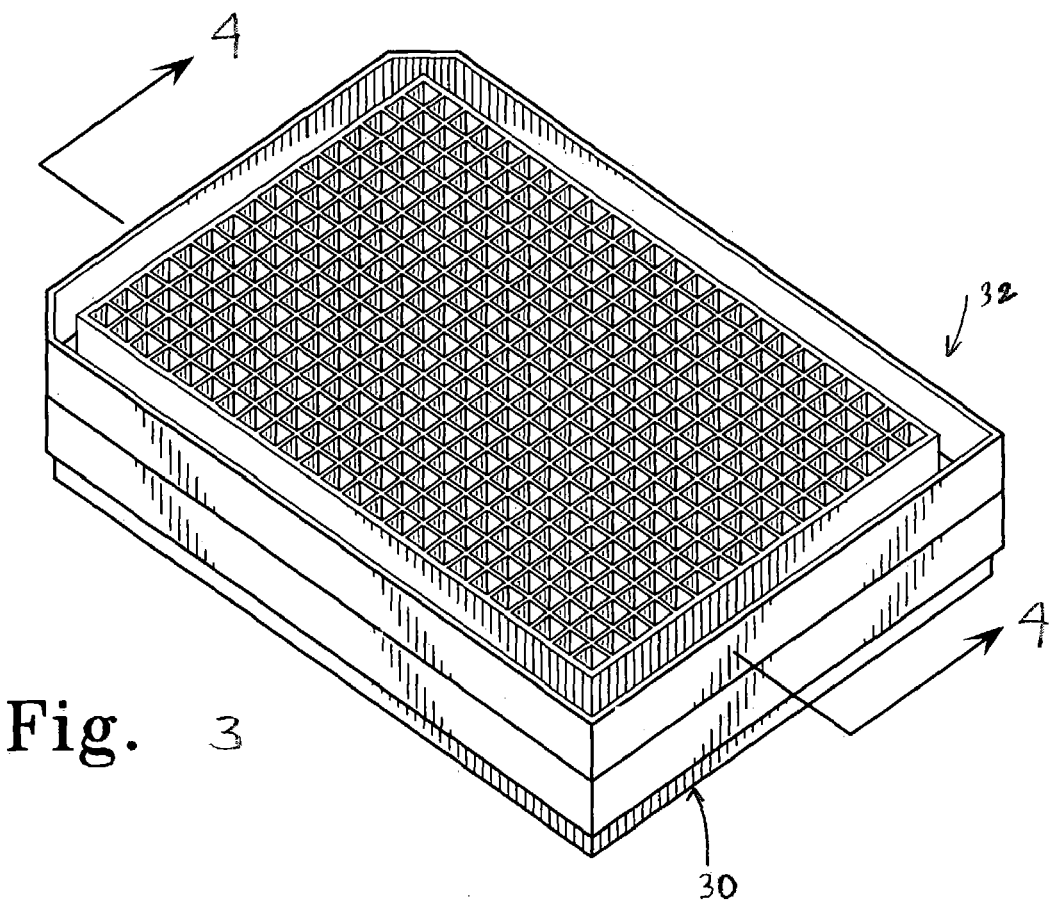
FIG. 3 is a perspective view of the multiwell plate of FIG. 2 shown in a stacked configuration with a second, similarly configured multiwell plate.

To counteract the effects of evaporation of sample material from the wells of multiwell plates, the present invention provides a novel configuration for each of the multiwell plates in a stacked (or unstacked) configuration of two or more plates such that the arrangement of one plate on top of another creates a substantial evaporation barrier to prevent air entrance to the wells of the lower plate to minimize evaporation of sample liquids in the wells when the plates are placed in the stacked configuration. Referring now to FIG. 2, there is shown one embodiment of multiwell plate 30 according to the teachings of the present invention. Plate 30 is preferably configured to be placed in a stacked configuration with one or more additional multiwell plates 32 as shown, for example, in perspective view in FIG. 3. Each of plates 30 and 32 in the stacked pair has the same general configuration as the other plate and thus only the configuration of plate 30 will be described for the sake of convenience. It is to be understood, of course, that the teachings of the present invention can be applied to one or more multiwell plates whether stored individually (e.g., unstacked) or placed into a stacked configuration with one or more additional multiwell plates.

Plate 30 includes a plurality of wells 34 for the receipt of samples (whether in an immobilized format or liquid form) therein. There can be any number of sample material stored in wells 34 of plate 30. There may be any number of wells in plate 30 arranged in any particular configuration of the wells, although 96 and 384 well plates are currently known and commercially available as described above. In FIG. 2, a 384 well plate is illustrated, merely for exemplary purposes. Multiwell plate 30 includes opposing, upstanding side walls 36 which extend around the border of the plate 30. In the present embodiment, there are four side walls 36 since the plate is in the overall shape of a rectangle. However, the plate may be fabricated in any other practicable configuration such as oval-shaped, trapezoidal, and the like.

Side walls 36 extend around the plate 30 and define a ridge or channel 38 spaced inwardly of the side walls 36 and extending around the plate between the side walls 36 and the plurality of wells 34 as best seen, for example, in FIG. 4. Ridge 38 thereby forms a border around the wells in the interior of the plate. As shown in the drawings, the ridge 38 is recessed below the level of the openings into wells 34 and optionally can extend down to the level of the lower surface of the openings in the wells 34 (as best shown in FIG. 4, for example) to define a substantial volumetric area where a liquid, such as water, buffer, or the like, can be introduced to create an evaporation barrier to substantially prevent air flow to the wells as is described below. Although the depth of the ridge or channel 38 is shown to be substantially equivalent to the depth of the various wells 34, it is to be understood that the depth of the ridge 38 can be varied to accommodate different volumes of fluid as desired. In a preferred aspect of the invention, the multiwell plate 30 (and plate 32) can also include a downwardly extending flange 40 (as best shown in FIG. 4) which extends entirely around a lower surface of the plate and which is configured to be removably received by ridge 38 of second multiwell plate in a mating relationship when plate 30 is positioned on top of a second plate in a stack. For example, as shown in FIGS. 4 and 5, when plate 32 is positioned on top of plate 30 in a stacked configuration, flange 40 of upper plate 32 extends at least partially into ridge 38 of lower plate 30 in a mating configuration. Flange 40 forms a border around a lower surface of plate 30 (and plate 32) and has four sides, each of which extends downwardly and is spaced slightly inwardly of an adjacent side wall 36 of the multiwell plate 30 in order to mate with a corresponding ridge 38 of a second similar plate. When a liquid is introduced into the ridge 38, contact of the flange 40 of plate 32 with the liquid in ridge 38 of plate 30 creates a substantial evaporation barrier to prevent air exchange to the wells 34 of multiwell plate 30 which helps to substantially eliminate evaporation of liquids contained therein when the plates are placed in the stacked configuration. The flange 40, when placed in the ridge 38 of the multiwell plate 30 and made to contact the liquid contained therein as shown in FIG. 5, increases the vapor diffusion path length to the internal wells of the plate 30 and thereby slows evaporation of the buffer or other sample liquids contained within those wells. The flange 40 could also be dimensioned to extend below the liquid level in the ridge 38, thus forming a "waterlock", substantially preventing air movement to the peripheral wells of the multiwell plate 30 until the water in the ridge evaporates below the level of the flange.

Although flange 40 is shown in the figures to be dimensioned with a width which extends to about the full length of the inside diameter of ridge 38 to provide a relatively conformal mating relationship, it is to be appreciated that the width (and depth) of flange 40 can be varied to extend less than about the length of the inside diameter of ridge 38, such as, for example, about 75% of the inside diameter of the ridge, for example about 50% or less of the inside diameter of the ridge 38. By having the flange 40 extend only about 75% or less of the inside diameter of corresponding ridge 38 of a second plate leaves sufficient space for liquid contained within the ridge 38 to extend around the sides of the flange to minimize spilling over of the liquid into peripheral wells of the plate.

The liquid introduced into the ridge 38 can comprise water, buffer, or other suitable liquid which becomes a substantial evaporation barrier when the plates are stacked to substantially prevent air entrance to the wells to minimize evaporation of liquids in the wells. The liquid within the ridge must evaporate substantially completely before there will be substantial evaporation of the sample liquid contents within the wells of the multiwell plate. The step of at least partially filling the ridge with a liquid step can be performed either before or after multiwell plate 32 is removably positioned on multiwell plate 30. As shown in FIGS. 6 and 7, an alternative multiwell plate embodiment 50 is shown which includes ridge 52 which is provided with a plurality of spaced-apart ribs 54 which extend upwardly of the lower surface of ridge 52 and are located in a staggered configuration on opposite sides of the ridge 52. Ribs 54 help to minimize sloshing of the liquid contained within the ridge 52 and add structural strength to the multiwell plate 50. The upwardly extending ribs 52 preferably have a height which is less than a height of the opposing side walls 56 of the plate 50 so that corresponding flange from a second multiwell plate (not shown in FIGS. 6 and 7) can fit within channel 58 when the plates are positioned in a stacked configuration. The ribs can be provided in any suitable configuration, such as the staggered configuration of FIG. 6, or the ribs can be spaced-apart on the same side of the channel as each of the other ribs. The ribs help to minimize sloshing of liquid contained within the ridge during operation of the HTS system, for example, and further add structural strength and rigidity to the multiwell plate.

Figure 9:
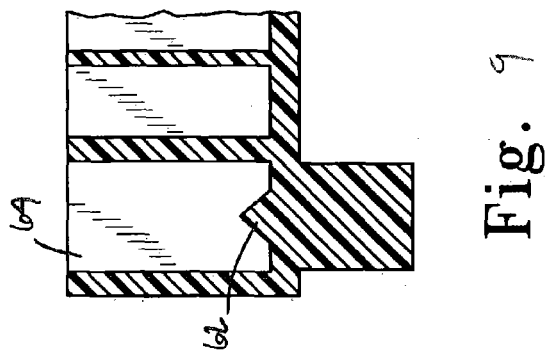
FIG. 9 is a is an enlarged, partial cross-sectional view taken along the line 9—9 in FIG. 8, with a partial sectional view of one corner thereof.
Figure 8:
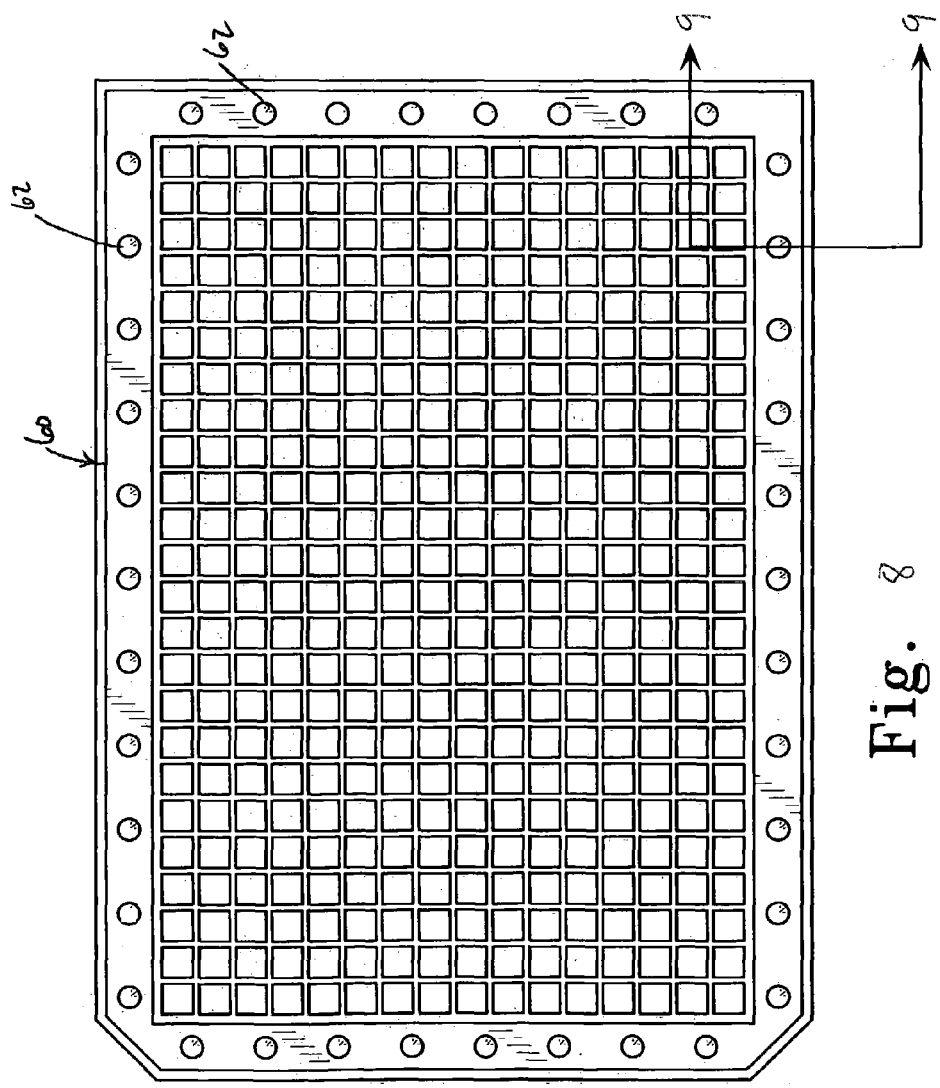
FIG. 8 is a top view of an alternative embodiment of the invention showing a plurality of upstanding projections or fingers extending from a lower surface of the channel of the multiwell plate of FIG. 2.

Further alternatively, in another embodiment of the present invention shown in FIGS. 8 and 9, a multiwell plate 60 can be provided similar to the above described multiwell plates which can include a plurality of small, upstanding projections or fingers 62 (which can be formed as an integral part of the plastic mold used to manufacture the plate 60), which extend upwardly from the lower surface of ridge 64 and which can help to break up fluid motion within the ridge 64 to help prevent sloshing of the liquid within the wells of the plate during handling of the plates during operation of HTS system 10, for example. In addition, fingers 62 can provide a substantial surface area for wicking of liquid upwards within the ridge to further reduce evaporation of liquid from the ridge. Further alternatively, the ridge, or the ribs or fingers extending within the ridge, can be provided with a layer of at least one wicking material covering at least a portion of the ridge (or ribs or fingers) such as a felt material, or a layer of absorbent material covering at least a portion of the ridge (or ribs or fingers), to further minimize the tendency for liquid sloshing, and which when wetted can to help reduce evaporation of sample material from the wells of the multiwell plates of the present invention.

In accordance with the principles of the present invention, significant improvements over currently known and available multiwell plate assemblies are provided. Most importantly, the present invention eliminates or substantially reduces the problem of excessive evaporation of sample material that occurs in multiwell plates, especially when two or more plates are stacked on top of one another as they typically are for use in HTS systems. Sample liquid loss, particularly in the corner or peripheral wells of stacked multiwell plates, may be substantially reduced over current multiwell plate configurations. The device and methods of the present invention are economically and easily manufactured since a single mold can be used to manufacture each of the multiwell plates to be used in the plate stack.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. Although the multiwell plates described above are shown to include only a single channel which extends around the border of the plate, the multiwell plate can include one or more additional channels or reservoirs so that, for example, any liquid displaced from the outer channel is contained and does not spill over into the wells of the multiwell plate. The additional channels or reservoirs could also provide a visual indication of when the outer channel was completely filled, since the presence of liquid within the additional channel or reservoir would indicate to the user that the outer channel had been substantially completely filled. Also, the additional channels or reservoirs could provide an overflow barrier to prevent liquid from spilling into the wells when two plates are stacked one on tope of the other and the flange is placed into contact with liquid within the outer ridge. In addition, although the above described multiwell plates are shown to include only a single continuous channel which extends around the entire periphery of the multiwell plate, it is to be appreciated that the ridge need not be continuous, but may be provided in any suitable configuration which would then be configured to receive a corresponding mating flange from a second multiwell plate to allow the plates to be stacked on top of another. All publications and patent documents cited in this application are incorporated by reference in their entirety for all purposes to the same extent as if each individual publication or patent document were so individually denoted.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of reducing evaporation from one or more wells of a first multiwell plate that is configured to be placed into a stacked configuration with a second multiwell plate having the same general configuration as the first multiwell plate, the method comprising:
   providing each of the first and the second multiwell plates with a plurality of blind wells and opposing side walls that extend around the plate and that define a ridge spaced inwardly of the side walls and extending around the plate between the side walls;
   providing each of the first and the second multiwell plates with a downwardly extending flange that extends around a lower surface of the plate;
   at least partially filling the ridge of the first multiwell plate with a liquid; and
   removably positioning the second multiwell plate on the first multiwell plate such that the flange of the second multiwell plate extends at least partially into the ridge of the first multiwell plate and contacts the liquid to thereby create a substantial evaporation barrier to prevent air entrance to the wells of the first multiwell plate to minimize evaporation of sample liquids in the wells when the second multiwell plate is positioned on the first multiwell plate.

2. The method of claim 1 wherein the at least partially filling the ridge with a liquid comprises at least partially filling the ridge with water.

3. The method of claim 1 wherein the at least partially filling the ridge with a liquid comprises at least partially filling the ridge with a buffer solution.

4. The method of claim 1 wherein said at least partially filling the ridge with a liquid is performed before said at least second multiwell plate is removably positioned on said at least first multiwell plate.

5. The method of claim 1 further including providing a lower surface of said ridge of said first multiwell plate with a plurality of spaced-apart ribs that extend upwardly from the ridge.

6. The method of claim 5 wherein said upwardly extending ribs have a height which is less than a height of said opposing side walls of said at least first multiwell plate.

7. The method of claim 1 wherein said ridge includes a layer of at least one wicking material covering at least a portion of said ridge.

8. The method of claim 7 wherein said at least one wicking material comprises a felt material.

9. The method of claim 1 wherein said ridge comprises a layer of absorbent material covering at least a portion of the ridge.

* * * * *